United States Patent
Yun et al.

(10) Patent No.: US 9,662,197 B2
(45) Date of Patent: May 30, 2017

(54) ARTIFICIAL MUSCLE

(71) Applicant: ELECTRONICS AND TELECOMMUNICATIONS RESEARCH INSTITUTE, Daejeon (KR)

(72) Inventors: Sung Ryul Yun, Daejeon (KR); Ki Uk Kyung, Daejeon (KR); Sae Kwang Nam, Daejeon (KR); Bong Je Park, Daejeon (KR); Sun Tak Park, Incheon (KR)

(73) Assignee: ELECTRONICS AND TELECOMMUNICATIONS RESERACH INSTITUTE, Daejeon (KR)

( * ) Notice: Subject to any disclaimer, the term of this patent is extended or adjusted under 35 U.S.C. 154(b) by 24 days.

(21) Appl. No.: 14/817,386

(22) Filed: Aug. 4, 2015

(65) Prior Publication Data
US 2016/0206420 A1    Jul. 21, 2016

(30) Foreign Application Priority Data

Jan. 15, 2015 (KR) .......... 10-2015-0007345

(51) Int. Cl.
*A61F 2/08* (2006.01)
*B25J 9/10* (2006.01)
*A61F 2/50* (2006.01)

(52) U.S. Cl.
CPC .......... *A61F 2/08* (2013.01); *B25J 9/1075* (2013.01); *A61F 2002/0894* (2013.01); *A61F 2002/5066* (2013.01); *A61F 2210/0014* (2013.01); *A61F 2210/0057* (2013.01); *A61F 2210/0066* (2013.01); *A61F 2230/0069* (2013.01); *A61F 2250/0002* (2013.01)

(58) Field of Classification Search
CPC .......... A61F 2/08; A61F 2002/0894; A61M 2025/0058
See application file for complete search history.

(56) References Cited

U.S. PATENT DOCUMENTS 5,389,222 A * 2/1995 Shahinpoor ............. F03G 7/005
204/616
2014/0085865 A1    3/2014 Yun et al.

FOREIGN PATENT DOCUMENTS

| JP | 2006-203982 | 8/2006 |
| JP | 2006-297005 | 11/2006 |
| JP | 2009-366 | 1/2009 |

(Continued)

*Primary Examiner* — Brian Dukert
(74) *Attorney, Agent, or Firm* — Kile Park Reed & Houtteman PLLC

(57) ABSTRACT

Provided herein is an artificial muscle capable of being miniaturized, realizing precision movement, and performing selective relaxation/contraction deformation according to the power output necessary in the muscle, the muscle including a first operation unit that includes electro-active polymer where relaxation-deformation occurs based on electric energy being applied; a heating unit that generates heat energy based on the electric being applied; a second operation unit that has a yarn structure and where contraction-deformation occurs based on the heat energy generated in the heating unit; and a control unit that applies electric energy to the first operation unit and the heating unit.

19 Claims, 6 Drawing Sheets

(56) References Cited

FOREIGN PATENT DOCUMENTS

| | | |
|---|---|---|
| KR | 10-2005-0003689 | 1/2005 |
| KR | 10-2011-0105501 | 9/2011 |
| KR | 10-1365108 | 2/2014 |
| KR | 10-2014-0103092 | 8/2014 |
| WO | 2009/145388 | 12/2009 |

\* cited by examiner

FIG. 9
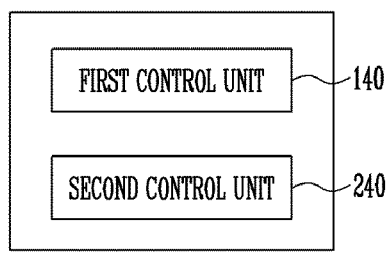
FIG. 10A  FIG. 10B
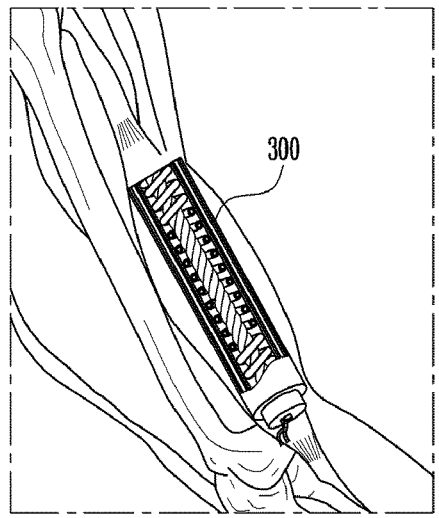 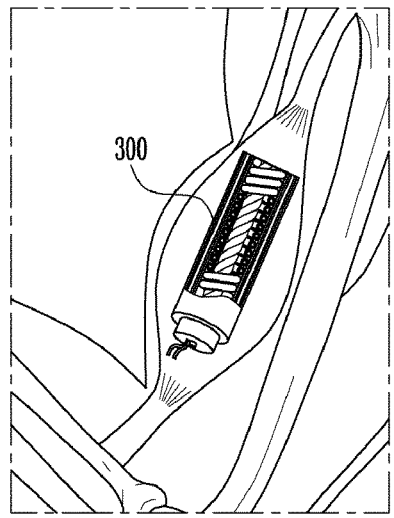

ARTIFICIAL MUSCLE

CROSS-REFERENCE TO RELATED APPLICATION

The present application claims priority to Korean patent application number 10-2015-0007345 filed on Jan. 15, 2015, in the Korean Intellectual Property Office, the entire disclosure of which is incorporated by reference herein.

BACKGROUND

1. Field

Various embodiments of the present disclosure relate to an artificial muscle, and more particularly, to a biomimic artificial muscle capable of mimicking characteristics of a human muscle that is in charge of movements of a human body.

2. Description of Related Art

An artificial muscle refers to a drive material or apparatus having similar drive characteristics and physical attributes as a muscle that is in charge of movements of a human body. The ultimate purpose of such an artificial muscle is to make it as similar as possible to an actual muscle of a human body, so that the artificial muscle can be used as a substitute for the actual muscle.

Currently, there are two types of artificial muscles: those that use oil pressure, and others that use SMA (shape memory alloy).

An artificial muscle that uses oil pressure has excellent response characteristics but it needs large pneumatic equipment in order to provide high performance, and thus it cannot be miniaturized.

On the other hand, an artificial muscle that uses SMA (shape memory alloy) offers great power output, but since its operation is based on transformation by heat, it may react sensitively to external temperatures. Therefore, this type of artificial muscle cannot provide excellent resistance to environments, and it is difficult to be precision-controlled, making it impossible to realize precision movements.

Therefore, there is a need for research and development on a new type of artificial muscle that can be miniaturized and that can realize precision movements.

SUMMARY

The purpose of the present disclosure is to resolve the aforementioned problems, that is, to provide an artificial muscle that may be miniaturized, realize precision movements, and selectively relax or contract according to the necessary power output of a muscle.

An embodiment of the present disclosure provides an artificial muscle including a first operation unit that includes an electro-active polymer where relaxation-deformation occurs based on electric energy being applied; a deformation restoration unit that restores that first operation unit that was relaxation-deformed; and a first control unit that applies the electric energy.

Herein, the first operation unit may include an electro-active polymer layer that includes the electro-active polymer; an upper and lower electrode layer that are disposed on an upper part and lower part of the electro-active polymer layer, respectively, and that receive the electric energy; and an upper and lower insulation layer that are disposed on an upper part of the upper electrode layer and on a lower part of the lower electrode layer, respectively, and that insulate the upper electrode layer and the lower electrode layer, respectively.

Herein, the electro-active polymer layer may include at least one thin film type electro-active polymer layer.

Herein, the first operation unit may have a shape of a tube.

Herein, the deformation restoration unit may be disposed inside the first operation unit, and includes a spring.

Herein, the first control unit may include a first sensing unit that senses an amount of deformation of the first operation unit; and a first power adjustment unit that adjusts the electric energy based on the sensed amount of deformation of the first sensing unit.

Another embodiment of the present disclosure provides an artificial muscle including a heating unit that generates heat energy based on electric energy being applied; a second operation unit having a yarn structure where contraction-deformation occurs based on the heat energy generated in the heating unit; and a second control unit that applies the electric energy.

Herein, the heating unit may include a spring.

The second operation unit may be disposed inside the heating unit.

The spring may have a hollow shape that allows a cooling fluid to flow.

The second control unit may include a second sensing unit that senses an amount of deformation of the second operation unit; and a second power adjustment unit that adjusts the electric energy based on the sensed amount of deformation of the second sensing unit.

Another embodiment of the present disclosure provides an artificial muscle including a first operation unit that includes electro-active polymer where relaxation-deformation occurs based on electric energy being applied; a heating unit that generates heat energy based on the electric energy being applied; a second operation unit having a yarn structure where contraction-deformation occurs based on the heat energy generated in the heating unit; and a control unit that applies the electric energy to the first operation unit and the heating unit.

The first operation unit may include an electro-active polymer layer that includes the electro-active polymer; an upper and lower electrode layer that are disposed on an upper part and a lower part of the electro-active polymer layer, respectively, and that receive the electric energy; and an upper and lower insulation layer that are disposed on an upper part of the upper electrode layer and a lower part of the lower electrode layer, respectively, and that insulate the upper electrode layer and the lower electrode layer, respectively.

The electro-active polymer layer may include at least one thin film type electro-active polymer layer.

The first operation unit may have a shape of a tube.

The heating unit may be disposed inside the first operation unit, and comprises a spring.

The second operation unit may be disposed inside the heating unit.

The spring may have a hollow shape that allows a cooling fluid to flow.

The spring may include a hollow cylindrical shape.

The control unit may include a first control unit that senses an amount of deformation of the first operation unit, and adjusts the electric energy being applied to the first operation unit based on the sensed amount of deformation of the first operation unit; and a second control unit that senses an amount of deformation of the second operation unit, and adjusts the electric energy being applied to the heating unit based on the sensed amount of deformation of the second operation unit.

An artificial muscle according to an embodiment of the present disclosure provides an effect of possibility of being miniaturized and further improving flexibility due to a first operation unit and a second operation unit configured based on polymer material and/or nano material having excellent flexibility and elasticity.

An artificial muscle according to an embodiment of the present disclosure provides an effect of realizing precision movements, and enabling selective relaxation/contraction movements according to a necessary power output of a muscle due to a first operation unit configured to include an electro-active polymer that generates relaxation-deformation, a second operation unit configured based on a yarn structure that includes a polymer material and/or nano for generating contraction-deformation, and a control unit configured to selectively control relaxation/contraction movement of the first operation and second operation unit in response to a necessary power output of the muscle/

An artificial muscle according to an embodiment of the present disclosure provides an effect of being applicable to muscles (consisting of muscular fiber, motor nerves, motor centers, spins, and Golgi's bodies) or robots that are in charge of movements in a human body. Especially, an artificial muscle according to an embodiment of the present disclosure provides an effect of being applicable to recyclable medical devices, precision robots and life support robots.

BRIEF DESCRIPTION OF THE DRAWINGS

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey the scope of the example embodiments to those skilled in the art.

In the drawing figures, dimensions may be exaggerated for clarity of illustration. It will be understood that when an element is referred to as being "between" two elements, it can be the only element between the two elements, or one or more intervening elements may also be present. Like reference numerals refer to like elements throughout.

FIG. 9 is a block diagram of a control unit according to the embodiment of the present disclosure;

FIG. 10A is a view of the artificial muscle where relaxation-deformation occurs applied to an arm according to an embodiment of the present disclosure;

FIG. 10B is a view of the artificial muscle where contraction-deformation occurs applied to an arm according to an embodiment of the present disclosure.

DETAILED DESCRIPTION

Figure 1:
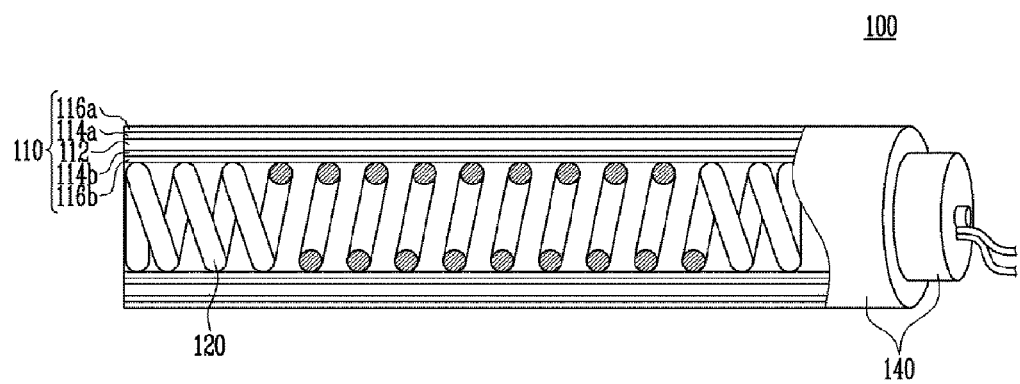
FIG. 1 is a cross-sectional view of an artificial muscle where relaxation-deformation occurs according to an embodiment of the present disclosure.

Hereinafter, embodiments will be described in greater detail with reference to the accompanying drawings. Embodiments are described herein with reference to cross-sectional illustrations that are schematic illustrations of embodiments (and intermediate structures). As such, variations from the shapes of the illustrations as a result, for example, of manufacturing techniques and/or tolerances, are to be expected. Thus, embodiments should not be construed as limited to the particular shapes of regions illustrated herein but may include deviations in shapes that result, for example, from manufacturing. In the drawings, lengths and sizes of layers and regions may be exaggerated for clarity. Like reference numerals in the drawings denote like elements.

Terms such as 'first' and 'second' may be used to describe various components, but they should not limit the various components. Those terms are only used for the purpose of differentiating a component from other components. For example, a first component may be referred to as a second component, and a second component may be referred to as a first component and so forth without departing from the spirit and scope of the present disclosure. Furthermore, 'and/or' may include any one of or a combination of the components mentioned.

Furthermore, a singular form may include a plural from as long as it is not specifically mentioned in a sentence. Furthermore, "include/comprise" or "including/comprising" used in the specification represents that one or more components, steps, operations, and elements exist or are added.

Furthermore, unless defined otherwise, all the terms used in this specification including technical and scientific terms have the same meanings as would be generally understood by those skilled in the related art. The terms defined in generally used dictionaries should be construed as having the same meanings as would be construed in the context of the related art, and unless clearly defined otherwise in this specification, should not be construed as having idealistic or overly formal meanings.

It is also noted that in this specification, "connected/coupled" refers to one component not only directly coupling another component but also indirectly coupling another component through an intermediate component. On the other hand, "directly connected/directly coupled" refers to one component directly coupling another component without an intermediate component. Furthermore, "on" in "on a layer or substrate" refers to one component not only directly formed on another component but also indirectly formed on another component through an intermediate component (for example, a third component). Furthermore, in this specification, "up", "upper", and "upper surface" of a component may also be "down", "lower", and "lower surface", respectively, of another component. That is, expressions of spatial directions must be understood as relative expressions, and should not be construed as limited to the absolute expressions.

The thicknesses of layers and areas in the drawings of this specification are exaggerated thicknesses for clarity of the layers and areas.

FIG. 1 is a cross-sectional view of an artificial muscle where relaxation-transformation occurs according to an embodiment of the present disclosure.

Referring to FIG. 1, the artificial muscle 100 where relaxation-transformation occurs according to the embodiment of the present disclosure includes a first operation unit 110, transformation restoration unit 120, and first control unit 140.

The first operation unit 110 may be connected to the first control unit 140 that will be explained later on. The first operation unit 110 may receive electric energy from the first control unit 140. The first operation unit 110 may include an electro-active polymer (EAP) where relaxation-transformation occurs based on the electric energy being applied.

The electro-active polymer (EAP) is a material where mechanical deformation occurs due to ion migration and diffusion, dipolar orientation or electrostatics when electric energy is applied. It may also mean a type of functional polymer that generates electric energy when mechanical deformation is applied.

In an example, examples of the electro-active polymer (EAP) that may be used in the present disclosure include an ionic EAP and electronic EAP.

Herein, the ionic EAP may refer to a polymer that contracts or expands due to ion migration or expansion, when electric energy is applied. Furthermore, examples of the ionic EAP that may be used include electrorheological fluid (ERF), carbon nanotube (CNT), conductive polymer (CP), ionic polymer metal composite (IPMC) and ionic polymer gel (IPG).

Herein, the electronic EAP may refer to a polymer that contracts or expands due to the polarization phenomenon that occurs when electric energy is applied. Furthermore, examples of the electronic EAP that may be used include liquid crystal elastomer (LCE), electro-viscoelastic elastomer, dielectric elastomer (EP), ferroelectric polymer, electro-strictive graft elastomer and electro-strictive paper.

In another example, the electronic EAP may include a dielectric that delivers polarity but cannot move an electron.

The first operation unit 110 may have the shape of a tube. That is, the first operation unit 110 may include a hollow. The tube and the hollow may include various shapes. In an embodiment, the tube and the hollow may include a cylindrical shape as illustrated in the drawings, but without limitation, and thus it may include a conic shape. In another example, the tube and the hollow may include a polyprismic shape such as a square prism, pentagonal prism, or hexagonal prism. In another example, the tube and the hollow may include a polypyramid shape such as a quadrangular pyramid, pentagonal pyramid, or hexagonal pyramid. In another example, the tube and the hollow may include a cylindroid shape or a cylindroid cone shape.

The deformation restoration unit 120 may restore the first operation unit 110 that was relaxation-deformed. That is, when the first operation unit 110 is relaxation-deformed, the deformation restoration unit 120 may restore the first operation unit 110 back to its original state.

The deformation restoration unit 120 may include a spring. That is, the deformation restoration unit 120 may include a restoration spring having a suitable rigidity considering the deformation force that may occur in the first operation unit 110, in order to quickly restore the first operation unit 110 where the relaxation-deformation occurred back to its original state. However, there is no limitation to the restoration spring. That is, the deformation restoration unit 120 may include any type of spring as long as it is capable of restoring the first operation unit 110 back to its original state. Especially, the diameter of the spring used herein may be adjusted depending on the purpose of use of artificial muscle according to the embodiment of the present disclosure.

In an embodiment, the spring may include a metal spring having a metallic material that is advantageous for elasticity restoration after deformation. Examples of the metal spring that may be used include a steel (for example, carbon steel or alloy steel) spring and nonferrous metal (for example, copper alloy or nickel alloy) spring. In another example, the spring may include a non-metallic spring having excellent heat conductivity and rigidity. Examples of the non-metallic spring that may be used include a rubber spring, fluid (for example, air or liquid) spring and synthetic resin spring. In another example, the spring may be a coil spring, leaf spring, volute spring, helical spring, spiral spring, Belleville spring, washer spring, snap spring, or torsion bar spring. Examples of the coil spring that may be used include a helical compressive spring, helical extension spring, and helical torsion spring. The leaf spring may be a single leaf spring or a laminated leaf spring.

The deformation restoration unit 120 may be disposed inside the first operation unit 110. That is, when the first restoration unit 120 has the shape of a tube, the deformation restoration unit 120 may be disposed in the tube, that is, inside the hollow. In an example, the deformation restoration unit 120 may be disposed such that it contacts an inner surface of the tube. In another example, when the tube has the shape of a cylinder as illustrated, the deformation restoration unit 120 may be disposed inside the tube such that it contacts an inner circumference of the tube. Herein, the inner surface of the tube and the inner circumference of the tube may be a lower surface of a lower insulation layer 116b.

The first control unit 140 may be connected to the aforementioned first operation unit 110. The first control unit 140 may apply electric energy to the first operation unit 110. Especially, the first control unit 140 may apply the electric energy to an upper electrode layer 114a and lower electrode layer 114b of the first operation unit 110.

Figure 2A:
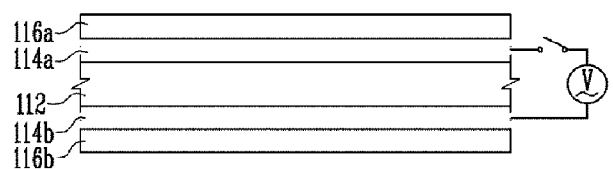
FIG. 2A is a cross-sectional view of a first operation unit before an electric energy is applied where the relaxation-deformation occurs according to the embodiment of the present disclosure.
Figure 2B:
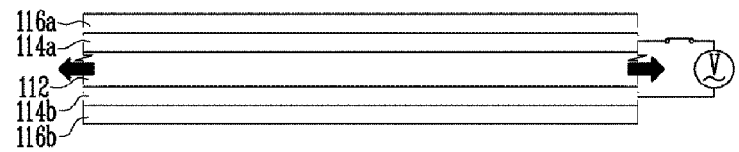
FIG. 2B is a cross-sectional view of a first operation unit after an electric energy is applied where the relaxation-deformation occurs according to the embodiment of the present disclosure.

FIGS. 2A and 2B are cross-sectional views of the first operation unit where relaxation-deformation occurs according to the embodiment of the present disclosure.

FIG. 2A is a cross-sectional view of the first operation unit before the electric energy is applied.

FIG. 2B is a cross-sectional view of the first operation unit after the electric energy is applied.

Referring to FIGS. 2A and 2B, the first operation unit 110 where the relaxation-deformation according to the embodiment of the present disclosure occurs may include an electro-active polymer layer 112, upper electrode layer 114a, lower electrode layer 114b, upper insulation layer 116a, and lower insulation layer 116b.

The electro-active polymer layer 112 may include an electro-active polymer where relaxation-deformation occurs based on electric energy being applied. However, the electro-active polymer layer 112 may include various materials having electro-active characteristics. The electro-active polymer is the same as the aforementioned electro-active polymer explained with reference to FIG. 1, and thus for the sake of conciseness, detailed explanation will be omitted.

The electro-active polymer layer 112 may especially include dielectric electro-active polymers. Such dielectric electro-active polymers are flexible, elastic, and have reversible transformation response characteristics due to the electric energy being applied, and its degree of transformation may be adjusted according to the size of the electric energy (for example, voltage) being applied.

The electro-active polymer layer 112 may include at least one thin film type electro-active polymer layer in order to improve deformation characteristics based on the electric energy being applied. In an example, the electro-active polymer layer 112 may consist of one thin film type electro-active polymer layer. In another example, the electro-active polymer layer 112 may consist of a plurality of laminated thin film type electro-active polymer layers. Herein, the thin film type electro-active polymer may include a material with excellent rigidity.

The upper electrode layer 114a and lower electrode layer 114b may be disposed on an upper and lower part of the electro-active polymer layer 112, respectively. That is, the upper electrode layer 114a may be disposed on an upper part of the electro-active polymer layer 112, and the lower electrode layer 114b may be disposed on a lower part of the electro-active polymer layer 112.

The upper electrode layer 114a and lower electrode layer 114b may be connected to the first control unit 140 that will be explained later on. The upper electrode layer 114a and lower electrode layer 114b may receive electric energy from the first control unit 140. Herein, the electric energy may include a voltage or current.

In an example, the upper electrode layer 114a may receive electric energy from the first control unit 140, while the lower electrode layer 114b is grounded. In another example, the upper electrode layer 114a may be grounded, while the lower electrode layer 114b receives electric energy from the first control unit 140. In another example, the upper electrode layer 114a and lower electrode layer 114b may receive electric energy of different sizes from the first control unit 140.

The upper electrode layer 114a and lower electrode layer 114b may include at least one electrode. In an example, the upper electrode layer 114a and lower electrode layer 114b may consist of one electrode. In another example, the upper electrode layer 114a and lower electrode layer 114b may consist of a plurality of electrodes. In a case where the upper electrode layer 114a and lower electrode layer 114b consist of a plurality of electrodes, the electrodes may receive electric energy of the same size or receive electric energy of different sizes from one another.

The upper electrode layer 114a and lower electrode layer 114b may use an electrode with excellent flexibility and an electrode structure that may guarantee flexibility so as to exhibit excellent durability even after repeated deformations.

The flexible electrode may include a nano-material based flexible electrode, but without limitation. That is, the upper electrode layer 114a and lower electrode layer 114b may use any electrode as long as it has flexibility.

Herein, the nano-material based flexible electrode may be realized based on a conductive complex material produced from a compound of conductive fillers having conductivity such as metal nano-particles, carbon nanotubes or carbon nano particles, and a rubber having high elasticity.

The flexible electrode may, without limitation, include a corrugated structure electrode, herringbone structure electrode, or mesh structure electrode. That is, the upper electrode layer 114a and lower electrode layer 114b may use any electrode as long as it has a flexible electrode structure.

As aforementioned, in the case of using an electrode with excellent flexibility and an electrode structure that may guarantee excellent electrode structure, when a size area of the electro-active polymer layer 112 disposed between the upper electrode layer 114a and lower electrode layer 114b contracts or expands, the size area of the upper electrode layer 114a and lower electrode layer 114b may contract or expand accordingly.

The upper electrode layer 114a and lower electrode layer 114b may include a transparent electrode. In an example, the transparent electrode may include an oxide transparent electrode, carbohydrate transparent electrode, metal type transparent electrode or hybrid-type transparent electrode. In another example, the transparent electrode may include an indium tin oxide (ITO) transparent electrode, zinc oxide (ZnO) transparent electrode, tin oxide ($SnO_2$) transparent electrode, polymer transparent electrode (for example, PEDOT:PSS(poly(3,4-ethylene dioxythiophene):poly(styrene sulfonate)) transparent electrode), carbon nanotube (CNT) transparent electrode, grapheme transparent electrode, silver nanowire transparent electrode, or a multilayered structure electrode.

The upper insulation layer 116a and lower insulation layer 116b may be disposed on an upper part of the upper electrode layer 114a and a lower part of the lower electrode layer 114, respectively. That is, the upper insulation layer 116a may be disposed on the upper part of the upper electrode layer 114a, and the lower insulation layer 116b may be disposed on the lower part of the lower electrode layer 114b.

The upper insulation layer 116a and lower insulation layer 116b may include at least one material of a material that may insulate the upper electrode layer 114a and lower electrode layer 114b, respectively, a material that may prevent discharging by electric energy being applied to the upper electrode layer 114 and lower electrode layer 114b, and a material of which the size area may contract or expand when the size area of the electro-active polymer layer 112 disposed between the upper electrode layer 114a and lower electrode layer 114b contracts or expands.

In an example, the upper insulation layer 116a and lower insulation layer 116b may include a same type of material as the material included in the electro-active polymer layer 112 in order to prevent deformation of the electro-active polymer layer 112 from being deteriorated. In another example, the upper insulation layer 116a and lower insulation layer 116b may include an elastic dielectric material having an elastic modulus lower than the material included in the electro-active polymer layer 112.

FIG. 2A is a cross-sectional view of the first operation unit 110 before the electric energy is applied, FIG. 2B is a cross-sectional view of the first operation unit 110 after the electric energy is applied.

When electric energy is not applied to the first operation unit 110, relaxation-transformation may not occur in the first operation unit 110 as illustrated in (a).

Then, when electric energy is applied to the first operation unit 110, relaxation-deformation may occur in the first operation unit 110 as illustrated in (b). That is, when electric energy is applied to the upper electrode layer 114a and lower electrode layer 114b, the size area of the electro-active polymer layer 112 may expand in a plane direction in response to the electric energy being applied, and the size area of the upper and lower electrode layer 114b and the upper and lower insulation layer 116b may expand in a plane direction in response to the electro-active polymer layer 112 expanding.

Then, when the electric energy being applied to the first operation unit 110 is reduced, the first operation unit 110 that was relaxation-transformed may be restored back to its original state as illustrated in (a). That is, when the electric energy being applied to the upper electrode layer 114a and lower electrode layer 114b is reduced, the expanded size of area of the electro-active polymer layer 112 may be reduced in a plane direction in response to the electric energy being reduced, and the expanded size of area of the upper lower electrode layer 114b and the upper part and lower insulation layer 116b may be reduced in a plane direction in response to the electro-active polymer layer 112 contracting. Herein, the first operation unit 110 that was relaxation-deformed may be quickly restored through the deformation restoration unit 120.

Figure 3:
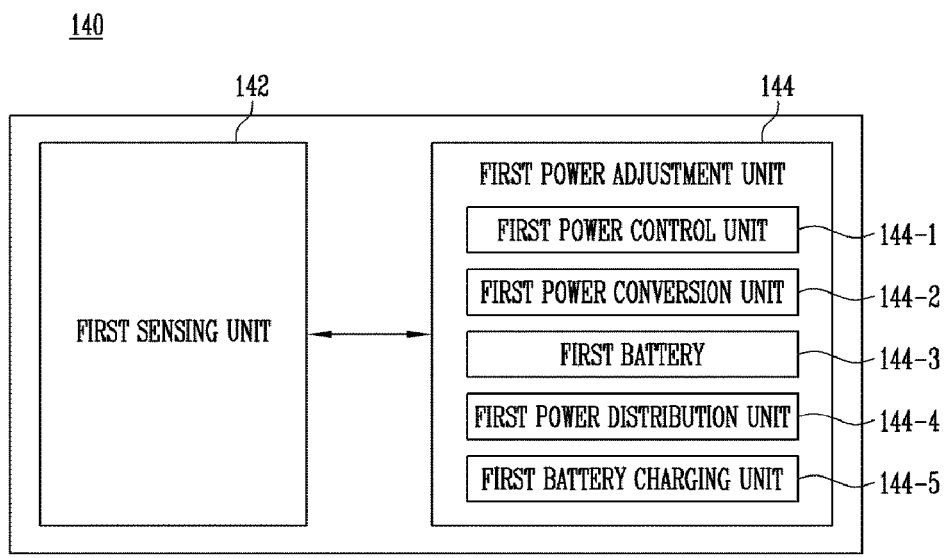
FIG. 3 is a block diagram of a first control unit according to the embodiment of the present disclosure.

FIG. 3 is a block diagram of the first control unit according to the embodiment of the present disclosure.

Referring to FIG. 3, the first control unit 140 according to the embodiment of the present disclosure may include a first sensing unit 142 and a first power adjustment unit 144.

The first sensing unit 142 may be connected to the first operation unit 110 and deformation restoration unit 120. The first sensing unit 142 may sense information on the first operation unit 110 and deformation restoration unit 120. In an example, the first sensing unit 142 may sense the information on the first operation unit 110 and deformation restoration unit 120 on a regular basis. In another example, the first sensing unit 142 may sense the information on the first operation unit 110 and deformation restoration unit 120 in real time. The first sensing unit 142 may convert the sensed information into electric signals, and provide the electric signals to the first power adjustment unit 144 that will be explained later on.

The information on the first operation unit 110 and deformation restoration unit 120 may include deformation amount information such as the length, shape, angle, and location of the first operation unit 110 and deformation restoration unit 120, and information on physical quantity such as the weight, temperature, heat, pressure and electricity quantity. Therefore, the first sensing unit 142 may include a limit sensor, pressure sensor, reed sensor, optical sensor, proximity sensor, ultrasound wave sensor, current sensor, temperature sensor, strain sensor, or heat sensor, but without limitation. The first sensing unit 142 may include any sensor that is capable of sensing information on the amount of deformation and physical quantity of the first operation unit 110 and deformation restoration unit 120.

The first sensing unit 142 may sense the amount of deformation of the first operation unit 110. The first sensing unit 142 may convert the amount of deformation of the first operation unit 110 into electric signals, and provide the electric signals converted from the amount of deformation of the first operation unit 110 to the first power adjustment unit 144 that will be explained hereinbelow.

The first power adjustment unit 144 is an apparatus or circuit configured to supply electric energy to the first operation unit 110, and there is no particular limitation to its configuration.

The first power adjustment unit 144 may be connected to the first sensing unit 142. The first power adjustment unit 144 may be provided with the electric signals converted from the sensed information from the first sensing unit 142. The first power adjustment unit 144 may adjust the electric energy based on the electric signals converted from the sensed information, and apply the adjusted electric energy to the aforementioned first operation unit 110.

Herein, the electric signals converted from the sensed information may include electric signals converted from the amount of deformation of the first operation unit 110.

Herein, the first power adjustment unit 144 may apply the adjusted electric energy to the upper electrode layer 114a and lower electrode layer 114b of the first operation unit 110.

The first power adjustment unit 144 may include a first power control unit 144-1, first power conversion unit 144-2, first battery 144-3, and first power distribution unit 144-4. The first power adjustment unit 144 may further include a first battery charging unit 144-5.

The first power control unit 144-1 may be connected to the first sensing unit 142. The first power control unit 144-1 may be provided with the electric signals converted from the sensed information from the first sensing unit 142. Herein, the electric signals converted from the sensed information may include electric signals converted from the amount of deformation of the first operation unit 110.

The first power control unit 144-1 may compare the electric signals converted from the sensed information with reference signals, and generate a first control signal according to the result of comparison. That is, the first power control unit 144-1 may generate the first control signal through a feedback control. The feedback control may include at least one control method of a proportional control (P control), integral control (I control), and differential control (D control). Furthermore, the first power control unit 144-1 may provide the first control signal to the first power conversion unit 144-2 that will be explained herein below.

The first power control unit 144-1 may generate the first control signal through the aforementioned feedback control, but there is no limitation, and thus any control method may be used.

The first power conversion unit 144-2 may be connected to the first power control unit 144-1 and first battery 144-3. The first power conversion unit 144-2 may be provided with the first control signal from the first power control unit 144-1. The first power conversion unit 144-2 may convert the power of the first battery 144-3 based on the first control signal, and generate electric energy that corresponds to the converted power. Herein, the first power conversion unit 144-2 may include a DC-DC converter. Herein, the electric energy may include a voltage or current. Furthermore, the first power conversion unit 144-2 may apply the electric energy to the first operation unit 110 or to the first power distribution unit 144-4 that will be explained herein below.

The first power distribution unit 144-4 may be connected to the first power conversion unit 144-2. The first power distribution unit 144-4 may be provided with electric energy from the first power conversion unit 144-2. The first power distribution unit 144-4 may distribute the electric energy and generate adjusted electric energies having different sizes. Herein, the first power distribution unit 144-4 may include a Switching Mode Power Supply (SNIPS). Furthermore, the first power distribution unit 144-4 may apply the adjusted electric energies to the first operation unit 110.

The first battery charging unit 144-5 may be connected to an external power source. The first battery charging unit 144-5 may be provided with charging energy from the external power source. Herein, the charging energy may include a current or voltage. Furthermore, the first battery charging unit 144-5 may charge the first battery 144-3 based on the charging energy.

Figure 4A:
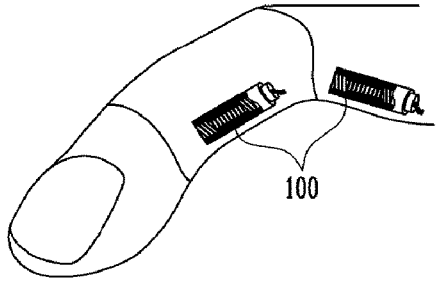
FIG. 4A is a view of the artificial muscle according to the embodiment of the present disclosure applied to a finger before a relaxation deformation occurs.
Figure 4B:
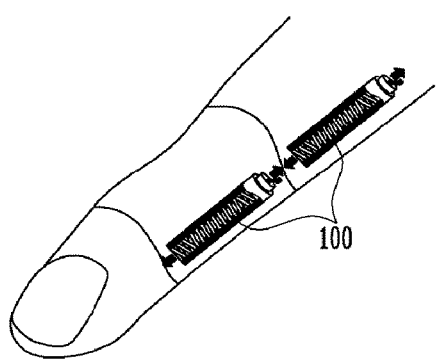
FIG. 4B is a view of the artificial muscle according to the embodiment of the present disclosure applied to a finger after a relaxation deformation occurs

FIGS. 4A and 4B illustrate views of the artificial muscle where relaxation-deformation occurs applied to a first control unit according to the embodiment of the present disclosure.

FIG. 4A is a view of the artificial muscle according to the embodiment of the present disclosure applied to a finger before the relaxation-deformation occurs, and FIG. 4B is a view of the artificial muscle according to the embodiment of the present disclosure applied to a finger after the relaxation-deformation.

Referring to FIGS. 4A and 4B, the artificial muscle 100 where the relaxation-deformation according to the embodiment of the present disclosure occurs may be used as a precision control type artificial muscle. That is, in the artificial muscle 100 where the relaxation-deformation according to the embodiment of the present disclosure occurs, the first operation unit 110 that includes the electro-active polymer layer 112 and the deformation restoration unit 120 that restores the first operation unit 110 may be combined, enabling relaxation-deformation and restoration to its original state, and thus the artificial muscle 100 may be applied to a human muscle where precision motion and small strength is needed, for example, a finger.

Herein, in order to realize various forms of precision motion of a human muscle such as a finger, the artificial muscle 100 where relaxation-deformation according to the embodiment of the present disclosure occurs may not only be disposed in plural number near a human muscle such as a finger, but the number of electro-active polymer layers 112 included in the first operation unit 110 or the properties of the electro-active polymer included in the electro-active polymer layer may be adjusted so as to generated various driving forces in response to the range of force being used in each area of the human muscle such as the finger.

Figure 5:
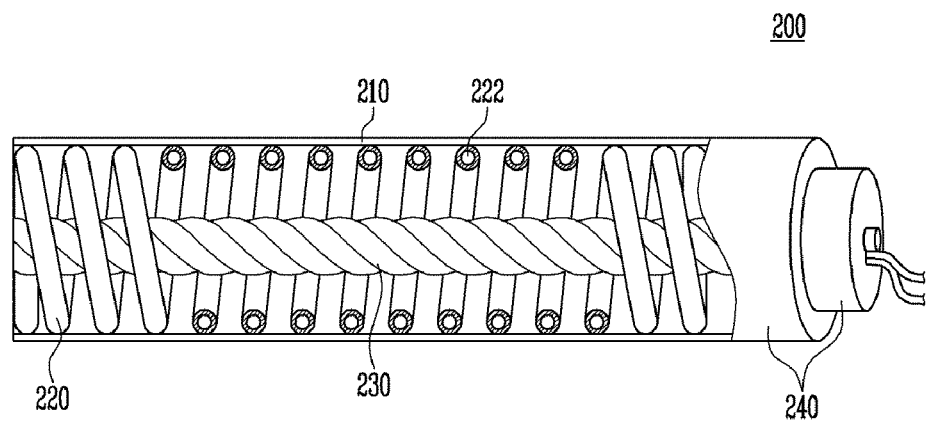
FIG. 5 is a cross-sectional view of an artificial muscle where contraction-deformation occurs according to an embodiment of the present disclosure.

FIG. 5 is a cross-sectional view of an artificial muscle where contraction-transformation occurs according to an embodiment of the present disclosure.

Referring to FIG. 5, the artificial muscle 200 where contraction-deformation occurs according to the embodiment of the present disclosure may further include a heating unit 220, second operation unit 230, and second control unit 240. It may also include an insulation unit (not illustrated).

The heating unit 220 may be connected to the second control unit 240 that will be explained later on. The heating unit 220 may be provided with electric energy from the second control unit 240. The heating unit 220 may generate heat energy based on the electric energy being provided. The heat energy generated by the heating unit 220 may be provided to the second operation unit 230 that will be explained later on. The heating unit 220 may include material having excellent conductivity.

That is, the heating unit 220 may generate contraction-deformation of the second operation unit 230. In other words, the heating unit 220 may convert the electric energy being applied from the second control unit 240 into heat energy, and the converted heat energy may be provided to the second operation unit 230 through the heating unit 220, and contraction-deformation may occur in the second operation unit 230 based on the heat energy provided from the heating unit 220.

Herein, the heating unit 220 may include a heating plate that may convert the electric energy being applied into heat energy, but without limitation. Thus, the heating unit 220 may include any type of apparatus or circuit as long as it may convert the electric energy being applied into heat energy. Furthermore, the heating unit 220 may restore the second operation unit 230 that was contraction-deformed. That is, when the second operation unit 230 is contraction-deformed, the heating unit 220 may restore the second operation unit 230 that was contraction-deformed back to its original state.

The heating unit 220 may include a spring. That is, the heating unit 220 may include a restoration spring that has a rigidity suitable for the deformation force that may be generated by the second operation unit 230 so as to quickly restore the second operation unit 230 where the contraction-transformation occurred based on the heat energy, but without limitation, and thus the heating unit 220 may include any type of spring as long as it may restore the second operation unit 230. Especially, the diameter of the spring may be adjusted and used according to the purpose of use of the artificial muscle according to the embodiment of the present disclosure. This spring is the same as the spring explained above with reference to FIG. 1, and thus detailed explanation will be omitted for the sake of conciseness.

The heating unit 220 may have the shape of a hollow 222 configured to allow a cooling fluid necessary for restoration of the deformation of the contraction-defirmed second operation unit 230 to flow. In an example, the heating plate may have the shape of a hollow configured to allow the cooling fluid to flow. In another example, the spring may have the shape of a hollow configured to allow the cooling fluid to flow.

That is, after the second operation unit 230 is contraction-deformed, the heating unit 220 may be cooled as the cooling fluid circulates through the hollow 222. Therefore, the second operation unit 230 that was heated and contraction-deformed may be restored back to its original state by the cooling induced in response to the heating unit 220 being cooled. Furthermore, the heating unit 220 may include a hollow cylindrical configured as a closed space, but without limitation. Thus, the heating unit 220 may include various structures that may reduce heat transfer rate in a certain direction. In an example, the heating plate may include a hollow cylindrical shape. In another example, the spring may include a hollow cylindrical shape.

A fluid such as cooling water, cooling oil or antifreeze, or a cooling gas may be used as the cooling fluid, but without limitation. Thus, any fluid having excellent heat transfer rate may be selected and used.

Furthermore, the heating unit 220 may further include a pump (not illustrated) at an end of the hollow 222 so that the cooling fluid may circulate through the hollow 222 continuously. The pump (not illustrated) may be controlled by the second control unit 240 that will be explained later on.

The insulation unit (not illustrated) may be formed on outer surface of the heating unit 220. The insulation unit (not illustrated) may include at least one material of a material that may insulate the heating unit 220, a material that may prevent the electric energy provided to the heating unit 220 from being discharged, and a material having flexibility so that its area size may contract or expand in response to a contraction or expansion of the heating unit 220 without mechanical damage.

In an example, the insulation unit (not illustrated) may include elastic dielectric material having a lower rigidity than the material included in the heating unit 220.

The second operation unit 230 may be provided with the heat energy generated by the heating unit 220. The second operation unit 230 may have a yarn structure where contraction-deformation may occur based on the heat energy generated by the heating unit 220. That is, as the second operation unit 230 has such a yarn structure, it may induce a strong contractile force.

The second operation unit 230 having a yarn structure may include at least one of polymer material and/or nano-material. The nano-material may include a carbon based nano-material, but without limitation. Herein, the carbon nano-material may include a carbon nanotube. The polymer material may include a conductive polymer material or polymer material possessing elasticity, but without limitation. That is, as the second operation unit 230 having the yarn structure is made with polymer material and/or nano-material, it may have an excellent contraction-deformation performance by the heat energy generated by the heating unit 220, and an excellent deformation restoring performance by the cooling fluid circulating through the hollow 222.

Herein, the second operation unit 230 having a yarn structure may adjust the range of the contraction force intended to be realized by adjusting the elastic modulus of the material (for example, nano-material and polymer material) that form the second operation unit 230 or by changing the density of the material (for example, nano-material and polymer material).

The second control unit 240 may be connected to the aforementioned heating unit 220. The second control unit 240 may apply electric energy to the heating unit 220.

Referring to FIG. 5, the aforementioned heating unit 220, the second operation unit 230 having a yarn structure and the second control unit 240 may be disposed inside the tube 210, that is, in the hollow of the tube 210.

The tube 210 may be made of a material having flexibility and elasticity. That is, as the tube 210 is made with a flexible and elastic material, when the area size of the second operation unit 230 having a yarn structure contracts or expands in a plane direction, in response, the area size of the tube 210 may contract or expand in the plane direction accordingly.

The tube 210 and hollow may include various shapes. In an example, the tube 210 and hollow may include a cylindrical shape as illustrated in the drawings, but there is no limitation thereto, and thus the tube 210 and hollow may include a cone shape. In another example, the tube 210 and hollow may include a polyprismic shape such as a square prism, pentagonal prism, or hexagonal prism. In another example, the tube and the hollow may include a polypyramid shape such as a quadrangular pyramid, pentagonal pyramid, or hexagonal pyramid. In another example, the tube and the hollow may include a cylindroid shape or a cylindroid cone shape.

The heating unit 220 may be disposed inside the tube 210 that is in the hollow of the tube. In an example, the heating unit 220 may be disposed inside the tube or disposed such that it contacts an inner surface of the tube. In another example, in the case where the tube has a shape of a cylinder as illustrated, the heating unit 220 may be disposed inside the tube such that it contacts an inner circumference of the tube. The heating unit 220 may be a spring as illustrated.

The second control unit 240 may be disposed on a side of the tube 210.

The second operation unit 230 having a yarn structure 230 may be disposed inside the heating unit 220 (for example, spring).

Figure 6A:
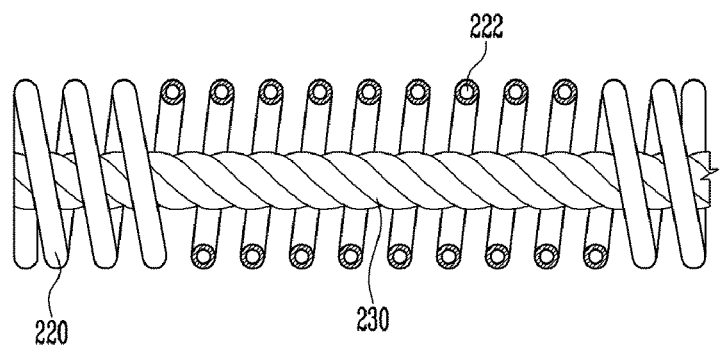
FIG. 6A is a cross-sectional view of a heating unit and a second operation unit before an electric energy is applied where the contraction-deformation occurs according to the embodiment of the present disclosure.
Figure 6B:
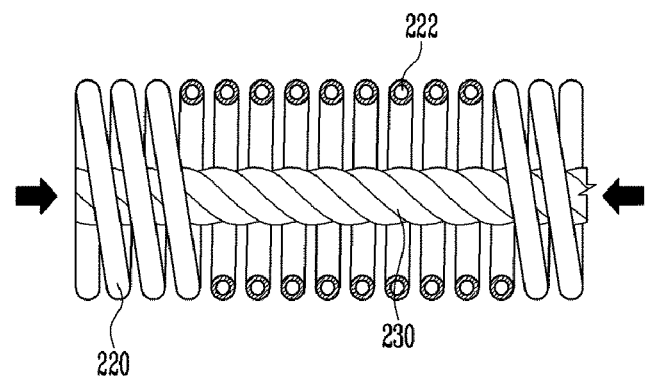
FIG. 6B is a cross-sectional view of a heating unit and a second operation unit after an electric energy is applied where the contraction-deformation occurs according to the embodiment of the present disclosure.

FIGS. 6A and 6B are cross-sectional views of the heating unit and the second operation unit where contraction-deformation occurs according to an embodiment of the present disclosure.

FIG. 6A is a cross-sectional view of the heating unit and second operation unit before the electric energy is applied, and FIG. 6B is a cross-sectional view of the heating unit and the second operation unit after the electric energy is applied.

Herein, the second operation unit 230 may have a yarn structure, as illustrated in the drawings.

When electric energy is not applied to the heating unit 220, the heating unit 220 will not generate heat energy, and thus contraction-deformation may not occur in the second operation unit 230 as illustrated in (a).

Then, when electric energy is applied to the heating unit 220, the heating unit 220 will generate heat energy, and thus contraction-deformation may occur in the second operation unit 230 as illustrated in (b). That is, when electric energy is applied to the heating unit 220, the heating unit 220 may generate heat energy in response to the electric energy being applied, and the area size of the second operation unit 230 may contract in a plane direction in response to the heat energy generated in the heating unit 220, and the area size of the heating unit 220 may contract in a plane direction in response to the second operation unit 230 contracting.

Then, when the electric energy being applied to the heating unit 220 is reduced, the second operation unit 230 that was contraction-deformed may be restored to its original state as illustrated in (a). That is, when the electric energy being applied to the heating unit 220 is reduced, the heat energy in the heating unit 220 may be reduced in response to the electric energy being reduced, and the area size of the contracted second operation unit 230 may expand in a plane direction in response to the heat energy being reduced in the heating unit 220, and the area size of the heating unit 220 may expand in the plane direction in response to the second operation unit 230 expanding, thereby quickly restoring the second operation unit 230. Herein, for the cooling necessary for a quick elastic restoration of the second operation unit 230, the heating unit 220 may allow a cooling fluid to flow through the hollow 222.

Figure 7:
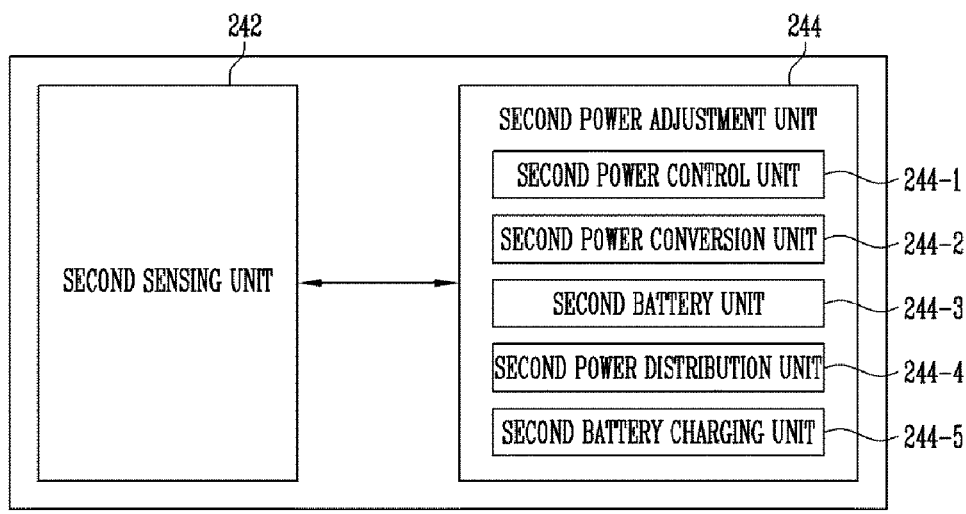
FIG. 7 is a block diagram of a second control unit according to an embodiment of the present disclosure.

FIG. 7 is a block diagram of the second control unit according to the embodiment of the present disclosure.

Referring to FIG. 7, the second control unit according to the embodiment of the present disclosure may include a second sensing unit 242 and a second power adjustment unit 244.

The second sensing unit 242 may be connected to the heating unit 220 and second operation unit 230. The second sensing unit 242 may sense information on the heating unit 220 and second operation unit 230. In an example, the second sensing unit 242 may sense the information on the heating unit 220 and the second operation unit 230 on a regular basis. In another example, the second sensing unit 242 may sense the information on the heating unit 220 and the second operation unit 230 in real time. The second sensing unit 242 may convert the sensed information into electric signals, and provide the electric signals converted from the sensed information to the second power adjustment unit 244 that will be explained later on.

The information on the heating unit 220 and the second operation unit 230 may include deformation amount information such as length information, shape information, angle information and location information, and physical quantity information such as weight information, temperature information, heat information, pressure information and electricity quantity information. Therefore, the second sensing unit 242 may include, a limit sensor, pressure sensor, reed sensor, optical sensor, proximity sensor, ultrasound sensor, current sensor, voltage sensor, temperature sensor, strain sensor, or heat sensor, but without limitation. Thus, the second sensing unit 242 may include any type of sensor as long as it is a sensor capable of sensing deformation amount information and physical quantity information of the heating unit 220 and the second operation unit 230.

The second sensing unit 242 may sense the amount of deformation of the second operation unit 230. The sensing unit 242 may convert the sensed amount of deformation of the second operation unit 230 into electric signals, and provide the electric signals converted from the amount of deformation to the second power adjustment unit 244 that will be explained hereinbelow.

The second power adjustment unit 244 is an apparatus or circuit configured to provide electric energy to the heating unit 220, and there is no particular limitation to its specific configuration.

The second power adjustment unit 244 may be connected to the second sensing unit 242. The second power adjustment unit 244 may receive the electric signals converted from the sensed information from the second sensing unit 242. The second power adjustment unit 244 may adjust the electric energy based on the electric signals converted from the sensed information, and apply the adjusted electric energy to the aforementioned heating unit 220.

Herein, the electric signals converted from the sensed information may include the electric signals converted from the amount of deformation of the second operation unit 230.

The second power adjustment unit 244 may include a second power control unit 244-1, second power conversion unit 244-2, second battery 244-3, and second power distribution unit 244-4. The second power adjustment unit 244 may further include a second battery discharging unit 244-5.

The second power control unit 244-1 may be connected to the second sensing unit 242. The second power control unit 244-1 may receive the electric signals converted from the sensed information from the second sensing unit 242. Herein, the electric signals converted from the sensed information may include electric signals converted from the amount of deformation of the second operation unit 230.

The second power control unit 244-1 may compare the electric signals converted from the sensed information, and generate a second control signal according to the comparison result. Feedback control may include at least one of control methods such as proportional control (P control), integral control (I control), and differential control (D control). Furthermore, the second power control unit 244-1 may provide the second control signal to the second power conversion unit 244-2 that will be explained later on.

The second power control unit 244-1 may generate the second control signal through the aforementioned feedback control, but without limitation, and thus the second power control unit 244-1 may use any control method.

The second power conversion unit 244-2 may be connected to the second power control unit 244-1 and the second battery 244-3. The second power conversion unit 244-2 may receive the second control signal from the second power control unit 244-1. The second power conversion unit 244-2 may convert the power of the second battery 244-3 based on the second control signal, and generate electric energy that corresponds to the converted power. Herein, the second power conversion unit 244-2 may include a DC-DC converter. Herein, the electric energy may include a current or voltage. Furthermore, the second power conversion unit 244-2 may apply electric energy to the heating unit 220, or provide it to the second power distribution unit 244-2 that will be explained later on.

The second power distribution unit 244-4 may be connected to the second power conversion unit 244-2. The second power distribution unit 244-4 may receive electric energy from the second power conversion unit 244-2. The second power distribution unit 244-4 may distribute the electric energy and generate adjusted electric energies having different sizes. Herein, the second power distribution unit 244-4 may include an SNIPS (Switching Mode Power Supply). Furthermore, the second power distribution unit 244-4 may apply the adjusted electric energies to the heating unit 220.

The second battery discharging unit 244-5 may be connected to an external power source. The second battery discharging unit 244-5 may receive charging energy from the external power source. Herein, the charging energy may include a current or voltage. Furthermore, the second battery charging unit 244-5 may charge the second battery 244-3 based on the charging energy.

Figure 8:
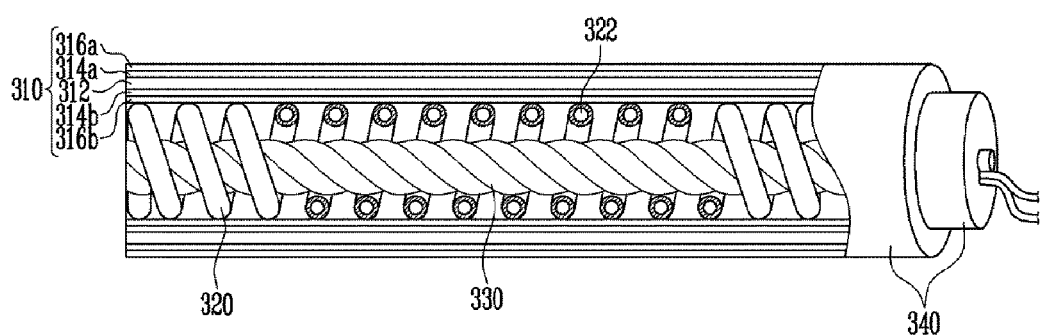
FIG. 8 is a cross-sectional view of an artificial muscle where relaxation/contraction-deformation occurs according to an embodiment of the present disclosure.

FIG. 8 is a cross-sectional view of an artificial muscle where relaxation/contraction deformation occurs according to an embodiment of the present disclosure.

Referring to FIG. 8, the artificial muscle 300 where relaxation/contraction deformation occurs according to the embodiment of the present disclosure includes a first operation unit 310, heating unit 320, second operation unit 330, and control unit 340.

Each of the first operation unit 310, heating unit 320, second operation unit 330 and control unit 340 corresponds to the first operation unit 110, deformation restoration unit 120/heating unit 220, second operation unit 230, and first control unit 140/second control unit 240, respectively, and thus explanation on the repeated configurations will be omitted for the sake of conciseness.

The first operation unit 310 may be connected to the control unit 340 that will be explained later on. The first operation unit 310 may receive electric energy from the control unit 340. The first operation unit 310 may include an electro-active polymer (EAP) where relaxation-deformation occurs based on the electric energy being applied. The electro-active polymer is the same as the electro-active polymer mentioned earlier on with reference to FIG. 1, and thus explanation on repeated configurations will be omitted for the sake of conciseness.

The first operation unit 310 may have a shape of a tube. That is, the first operation unit 310 may include a hollow. The tube and hollow are the same as the tube and hollow explained earlier on with reference to FIG. 1, and thus detailed explanation on repeated configurations will be omitted for the sake of conciseness.

The first operation unit 310 may include an electro-active polymer layer 312, upper electrode layer 314*a*, lower electrode layer 314*b*, upper insulation layer 316*a*, and lower insulation layer 316*b*.

The electro-active polymer layer 312 may include an electro-active polymer where relaxation-deformation occurs based on the electric energy being applied, but there is no limitation, and thus the electro-active polymer layer 312 may include various types of materials having electro-active properties.

The electro-active polymer layer 312 may include, especially, a dielectric electro-active polymer. Such dielectric electro-active polymers are flexible, elastic, and have reversible deformation response characteristics due to the electric energy being applied, and the degree of deformation of the dielectric electro-active polymers may be adjusted according to the amount of the electric energy being applied (for example, voltage).

The electro-active polymer layer 312 may include at least one thin film type electro-active polymer layer in order to improve the transformation characteristics based on the electric energy being applied. In an example, the electro-active polymer layer 312 may consist of one thin film type electro-active polymer. In another example, the electro-active polymer layer 312 may consist of a plurality of thin film type electro-active polymer layers stacked on the electro-active polymer layer 312. Herein, the electro-active polymer may include a material with excellent elastic modulus.

The upper electrode layer 314a and lower electrode layer 314b may be disposed on an upper part and lower part of the electro-active polymer layer 312, respectively. That is, the upper electrode layer 314a may be disposed on the upper part of the electro-active polymer layer 312, and the lower electrode layer 314b may be disposed on the lower part of the electro-active polymer layer 312.

The upper electrode layer 314a and the lower electrode layer 314b may be connected to the control unit 340 that will be explained later on. The upper electrode layer 314a and the lower electrode layer 314b may receive electric energy from the control unit 340. Herein, the electric energy may include a voltage or current.

In an example, the upper electrode layer 314a may receive electric energy from the control unit 340, and the lower electrode layer 314b may be grounded. In another example, the upper electrode layer 314a may be grounded, and the lower electrode layer 314b may receive electric energy from the control unit 340. In another example, the upper electrode layer 314a and lower electrode layer 314b may receive electric energy of different sizes.

The upper electrode layer 314a and lower electrode layer 314b may include one or more electrodes. In an example, the upper electrode layer 314a and lower electrode layer 314b may consist of one electrode. In another example, the upper electrode layer 314a and lower electrode layer 314b may consist of a plurality of electrodes. When the upper electrode layer 314a and lower electrode layer 314b consist of a plurality of electrodes, each of the plurality of electrodes may receive electric energy of the same size with one another or receive electric energy of different sizes.

The upper electrode layer 314a and lower electrode layer 314b may use an electrode with excellent flexibility and an electrode structure capable of guaranteeing flexibility so as to have excellent durability even after the electro-active polymer layer 312 is deformed repeatedly. The flexible electrode is the same as the flexible electrode mentioned above with reference to FIGS. 2A and 2B, and detailed explanation on the flexible electrode will be omitted for the sake of conciseness.

The upper electrode layer 314a and lower electrode layer 314b may include a transparent electrode. The transparent electrode is the same as the transparent electrode mentioned above with reference to FIGS. 2A and 2B, and thus detailed explanation on the transparent electrode will be omitted for the sake of conciseness.

The upper insulation layer 316a and lower insulation layer 316b may be disposed in an upper part of the upper electrode layer 314a and a lower part of the lower electrode layer 314b, respectively. That is, the upper insulation layer 316a may be disposed on the upper part of the upper electrode layer 314b, and the lower insulation layer 316b may be disposed on the lower part of the lower electrode layer 314b.

The upper insulation layer 316a and lower insulation layer 316b may include at least one material of a material that is capable of insulating the upper insulation layer 316a and lower insulation layer 316b, respectively, a material that is capable of preventing discharging by the electric energy applied to the upper electrode layer 314a and lower electrode layer 314b, a material of which the size contracts or expands in response to the size area of the electro-active polymer layer 312 disposed between the upper electrode layer 314a and lower electrode layer 314b contracting or expanding.

In an example, the upper insulation layer 316a and lower insulation layer 316b may include a same type of material as the material included in the electro-active polymer layer 312 in order to prevent the insulation layer from deteriorating deformation of the electro-active polymer layer 312. In another example, the upper insulation layer 316a and lower insulation layer 316b may include an elastic dielectric material having an elastic modulus lower than that of the material included in the electro-active polymer layer 312.

The first operation unit 310 may adjust a range of expansion force to be realized by adjusting the number of the electro-active polymer layers 312 or properties of the electro-active polymer included in the electro-active polymer layers.

The heating unit 320 may restore the first operation unit 310 that was relaxation-deformed. That is, when the first operation unit 310 is relaxation-transformed, the heating unit 320 may restore the first operation unit that was relaxation-deformed back to its original state. That is, the heating unit 320 may have the characteristics of the deformation restoration unit 120 mentioned earlier with reference to FIG. 1.

The heating unit 320 may be connected to the control unit 340 that will be explained later on. The heating unit 320 may receive electric energy from the control unit 340. The heating unit 320 may generate heat energy based on the electric energy being applied. The heat energy generated in the heating unit 320 may be provided to the second operation unit 330 that will be explained later on. The heating unit 320 may include a material having excellent heat conductivity. That is, the heating unit 320 may have the characteristics of the heating unit 220 mentioned above with reference to FIG. 5.

That is, the heating unit 320 may contraction-transform the second operation unit 330. In other words, the heating unit 320 may convert the electric energy being applied from the control unit 340 into heat energy, and the converted heat energy may be provided to the second operation unit 330 through the heating unit 320, and contraction-deformation may occur in the second operation unit 330 based on the heat energy provided from the heating unit 320.

Herein, the heating unit 320 may include a heating plate that may convert the electric energy being applied into heat energy, but there is no limitation thereto, and thus the heating unit 320 may include any apparatus or circuit as long as it may convert the electric energy being applied into heat energy.

Furthermore, the heating unit 320 may restore the second operation unit 330 that was contraction-deformed. That is, when the second operation unit 330 is contraction-deformed, the heating unit 320 may restore the second operation unit 330 that was contraction-deformed back to its original state.

The heating unit 320 may include a spring. That is, for a quick restoration of the second operation unit 330 where contraction-deformation has occurred based on the heat energy, the heating unit 320 may include a restoration spring having an appropriate rigidity in consideration of the deformation force that may be generated by the second operation unit 330. However, the heating unit 320 may include, without limitation, a restoration spring. That is, the heating unit 320 may include any type of spring that may restore the deformation of the second operation unit 330. Especially, the diameter of the spring may be adjusted and used according to the purpose of use of the artificial muscle according to the embodiment of the present disclosure. The spring is the same as the spring mentioned earlier on with reference to FIG. 1, and thus explanation on the spring will be omitted for the sake of conciseness.

The heating unit 320 may have the shape of a hollow 322 that may allow a cooling fluid to flow for the cooling necessary for the restoration of deformation of the second operation unit 330. In an example, the heating plate may have the shape of a hollow 322 that may allow the cooling fluid to flow. In another example, the spring may have the shape of a hollow that may allow the cooling fluid to flow.

That is, after the second operation unit 330 is contraction-deformed, the heating unit 320 may be cooled by the circulation of the cooling fluid through the hollow 322. Therefore, the second operation unit 330 that was heated and contraction-deformed may be cooled in response to the cooling of the heating unit 320 and be restored back to its original state Furthermore, the heating unit 320 may include a hollow cylinder having a closed space, but there is not limitation, and thus the heating unit 320 may include one of various structures that may reduce heat transfer in a certain direction. In an example, the heating plate may include a hollow cylinder shape. In another example, the spring may include a hollow cylinder.

The cooling fluid may be a fluid such as cooling water, cooling oil, or antifreeze, or cooling gas, but there is no limitation, and thus a fluid with excellent heat transfer rate may be used.

Furthermore, the heating unit 320 may further include a pump (not illustrated) at its end so that the cooling fluid may continuously circulate through the hollow. The pump (not illustrated) may be controlled by a control unit 340 that will be explained later on.

The insulation unit (not illustrated) may be formed on a surface of the heating unit 320. The insulation unit (not illustrated) may include at least one material of a material that may insulate the heating unit 320, a material that may prevent the electric energy being applied to the heating unit 320 from discharging, and a material having flexibility of which its area size of the heating unit 320 may contract or expand in response to the area size of the heating unit 320 contracting or expanding.

In an example, the insulation unit (not illustrated) may include an elastic dielectric material having a lower rigidity than the material included in the heating unit 320.

The second operation unit 330 may be provided with heat energy generated in the heating unit 320. The second operation unit 330 may have a yarn structure where contraction-deformation occurs based on the heat energy generated in the heating unit 320. That is, the second operation unit 330 may have the yarn structure so as to induce a strong contraction force.

The second operation unit 330 having a yarn structure may include at least one of polymer material and/or nano material. The nano material may include, without limitation, a carbon nano material. The polymer material may include, without limitation, a conductive polymer material or polymer material possessing elasticity. That is, the second operation unit 330 having the yarn structure is made of polymer material and/or nano-material, and thus has excellent contraction-deformation performance by the heat energy generated in the heating unit 320, and also excellent deformation restoration performance by the cooling of the cooling fluid that circulates in the hollow 322 of the heating unit 320.

Herein, the range of contraction force to be realized may be adjusted by adjusting the rigidity of the material (for example, nano-material or polymer material) that forms the second operation unit 330 having a yarn structure or by changing the density of the material that forms the second operation unit 330 (for example, nano-material or polymer material).

The control unit 340 may be connected to the aforementioned first operation unit 310 and heating unit 320. The control unit 340 may apply electric energy to the first operation unit 310. Especially, the control unit 340 may apply the electric energy to the upper electrode layer 314a and lower electrode layer 314b of the first operation unit 310. The control unit 340 may apply the electric energy to the heating unit 320.

Referring to FIG. 8, the first operation unit 310 may have a tube shape (for example, a cylindrical shape). The tube shape may have a cylindrical shape as illustrated.

The heating unit 320 may be disposed inside the first operation unit 310. That is, the heating unit 320 may be disposed inside the tube, that is, in the hollow of the tube in the case where the first operation unit 310 has a tube shape. In an example, the heating unit 320 may be disposed inside the tube, or such that it contacts the inside of the tube. In another example, when the tube has a cylindrical shape as illustrated, the heating unit 320 may be disposed such that it contacts the inner circumference of the tube. Herein, the inside of the tube and inner circumference of the tube may be a lower surface of the lower insulation layer 316b.

The control unit 340 may be disposed at one side of the first operation unit 310.

The second operation unit 330 having a yarn structure may be disposed inside the heating unit 320 (for example, the spring).

When electric energy is not applied to the first operation unit 310, relaxation-deformation may not occur in the first operation unit 310. Then, when electric energy is applied to the first operation unit 310, relaxation-deformation may occur in the first operation unit 310. That is, when electric energy is applied to the upper electrode layer 314a and the lower electrode layer 314b, the area size of the electro-active polymer layer 312 may expand in a plane direction in response to the electric energy being applied, and the area size of the upper and lower electrode layer 314a, 314b and the upper and lower insulation layer 316a, 316b may expand in a plane direction in response to the expanded electro-active polymer layer 312. Then, when the electric energy being applied to the first operation unit 310 is reduced, the first operation unit 310 that was relaxation-deformed may be restored back to its original state. That is, when the electric energy being applied to the upper electrode layer 314a and lower electrode layer 314b is reduced, the area size of the electro-active polymer layer 312 that expanded in the plane direction may be reduced in response to the electric energy being reduced, and the area size of the upper and lower electrode layer 314a, 314b and the upper and lower insulation layer 316a, 316b that expanded may be reduced in response to the electro-active polymer layer 312 contracting. Herein, the first operation unit 310 that was relaxation-deformed may be quickly restored through the heating unit 320 (for example, spring).

When electric energy is not applied to the heating unit 320, the heating unit 320 will not generate heat energy, and thus contraction-deformation may not occur in the second operation unit 330. Then, when electric energy is applied to the heating unit 320, the heating unit 320 may generate heat energy, and contraction-deformation may occur in the second operation unit 330. That is, when electric energy is applied to the heating unit 320, the heating unit 320 may generate heat energy in response to the electric energy being applied, the area size of the second operation unit 330 may contract in a plane direction in response to the heat energy generated in the heating unit 320, and the area size of the heating unit 320 may contract in a plane direction in response to the second operation unit 330 contracting. Then, when the electric energy being applied to the heating unit 320 is reduced, the second operation unit 330 that was contraction-deformed may be restored back to its original state. That is, when the electric energy being applied to the heating unit 320 is reduced, the heat energy in the heating unit 320 may be reduced in response to the electric energy being reduced, and the area size of the second operation unit 330 that contracted may expand in a plane direction in response to the heat energy being reduced in the heating unit 320, and the area size of the heating unit 320 may expand in a plane direction in response to the second operation unit 330 expanding, and thus the second operation unit 330 may be quickly restored. Herein, for the cooling necessary for a quick elasticity restoration of the second operation unit 330, the heating unit 320 may allow the cooling fluid to flow through the hollow 322.

FIG. 9 is a block diagram of the control unit according to the embodiment of the present disclosure.

Referring to FIG. 9, the control unit 340 according to the embodiment of the present disclosure may include a first control unit 140 and a second control unit 240.

Referring to FIGS. 3 and 9, the first control unit 140 may sense the amount of transformation of the first operation unit 310, adjust the electric energy being applied to the first operation unit 310 based on the sensed amount of deformation of the first operation unit 310, and apply the adjusted electric energy to the first operation unit 310.

The first control unit 140 may include a first sensing unit 142 and a first power adjustment unit 144.

The first sensing unit 142 may be connected to the first operation unit 310 and the heating unit 320. The first sensing unit 142 may sense information on the first operation unit 310 and the heating unit 320. In an example, the first sensing unit 142 may sense the information on the first operation unit 310 and the heating unit 320 on a regular basis. In another example, the first sensing unit 142 may sense the information on the first operation unit 310 and heating unit 320 in real time. The first sensing unit 142 may convert the sensed information into electric signals, and provide the electric signals converted from the sensed information to the first power adjustment unit 144 that will be explained later on.

The information on the first operation unit 310 and the heating unit 320 may include deformation amount information such as length information, shape information, angle information and location information, and physical quantity information such as weight information, temperature information, heat information, pressure information and electricity quantity information. Therefore, the first sensing unit may include, a limit sensor, pressure sensor, reed sensor, optical sensor, proximity sensor, ultrasound sensor, current sensor, voltage sensor, temperature sensor, transformation amount sensor, or heat sensor, but without limitation. Thus, the first sensing unit may include any type of sensor as long as it is a sensor capable of sensing deformation amount information and physical quantity information of the first operation unit 310 and the heating unit 320.

The first sensing unit 142 may sense the amount of deformation of the first operation unit 310. The first sensing unit 142 may convert the sensed amount of deformation of the first operation unit 310 into electric signals, and provide the electric signals converted from the amount of deformation of the first operation unit 310 to the first power adjustment unit 144 that will be explained hereinbelow.

The first power adjustment unit 144 is an apparatus or circuit configured to supply electric energy to the first operation unit 310, and there is no particular limitation to its configuration.

The first power adjustment unit 144 may be connected to the first sensing unit 142. The first power adjustment unit 144 may be provided with the electric signals converted from the sensed information from the first sensing unit 142. The first power adjustment unit 144 may adjust the electric energy based on the electric signals converted from the sensed information, and apply the adjusted electric energy to the first operation unit 310 mentioned earlier on.

Herein, the electric signals converted from the sensed information may include electric signals converted from the amount of deformation of the first operation unit 310.

Herein, the first power adjustment unit 144 may apply the adjusted electric energy to the upper electrode layer 314a and lower electrode layer 314b of the first operation unit 310.

The first power adjustment unit 144 may include a first power control unit 144-1, first power conversion unit 144-2, first battery 144-3, and first power distribution unit 144-4. The first power adjustment unit 144 may further include a first battery discharging unit 144-5.

The first power control unit 144-1 may be connected to the first sensing unit 142. The first power control unit 144-1 may be provided with the electric signals converted from the sensed information from the first sensing unit 142. Herein, the electric signals converted from the sensed information may include electric signals converted from the amount of deformation of the first operation unit 310.

The first power control unit 144-1 may compare the electric signals converted from the sensed information with reference signals, and generate a first control signal according to the result of comparison. That is, the first power control unit 144-1 may generate the first control signal through a feedback control. The feedback control may include at least one control method of a proportional control (P control), integral control (I control), and differential control (D control). Furthermore, the first power control unit 144-1 may provide the first control signal to the first power conversion unit 144-2 that will be explained later on.

The first power control unit 144-1 may generate the first control signal through the feedback control mentioned earlier on, but there is no limitation, and thus any control method may be used.

The first power conversion unit 144-2 may be connected to the first power control unit 144-1 and first battery 144-3. The first power conversion unit 144-2 may be provided with the first control signal from the first power control unit 144-1. The first power conversion unit 144-2 may convert the power of the first battery 144-3 based on the first control signal, and generate electric energy that corresponds to the converted power. Herein, the first power conversion unit 144-2 may include a DC-DC converter. Herein, the electric energy may include a voltage or current. Furthermore, the first power conversion unit 144-2 may apply the electric energy to the first operation unit 310 or to the first power distribution unit 144-4 that will be explained hereinbelow.

The first power distribution unit 144-4 may be connected to the first power conversion unit 144-2. The first power distribution unit 144-4 may be provided with the electric energy from the first power conversion unit 144-2. The first power distribution unit 144-4 may distribute the electric energy and generate adjusted electric energies of different sizes. Herein, the first power distribution unit 144-4 may include a Switching Mode Power Supply (SNIPS). Furthermore, the first power distribution unit 144-4 may apply the adjusted electric energies to the first operation unit 310.

The first battery charging unit 144-3 may be connected to an external power source. The first battery charging unit 144-3 may be provided with charging energy from the external power source. Herein, the charging energy may include a current or voltage. Furthermore, the first battery charging unit 144-3 may charge the first battery 144-3 based on the charging energy.

Referring to FIGS. 7 and 9, the second control unit 240 may sense the amount of transformation of the second operation unit 330, adjust the electric energy being applied to the heating unit 320 based on the sensed amount of deformation of the second operation unit 330, and apply the adjusted electric energy to the heating unit 320.

The second control unit 240 may include a second sensing unit 242 and a second power adjustment unit 244.

The second sensing unit 242 may be connected to the heating unit 320 and the second operation unit 330. The second sensing unit 242 may sense information on the heating unit 320 and the second operation unit 330. In an example, the second sensing unit 242 may sense the information on the heating unit 320 and the second operation unit 330 on a regular basis. In another example, the second sensing unit 242 may sense the information on the heating unit 320 and the second operation unit 330 in real time. The second sensing unit 242 may convert the sensed information into electric signals, and provide the electric signals converted from the sensed information to the second power adjustment unit 244 that will be explained later on.

The information on the heating unit 320 and the second operation unit 330 may include deformation amount information such as the length, shape, angle, and location of the heating unit 320 and the second operation unit 330, and information on physical quantity such as the weight, temperature, heat, pressure and electricity quantity. Therefore, the second sensing unit 242 may include, a limit sensor, pressure sensor, reed sensor, optical sensor, proximity sensor, ultrasound wave sensor, current sensor, temperature sensor, strain sensor, or heat sensor, but without limitation. The second sensing unit 242 may include any sensor that is capable of sensing information on the amount of transformation and physical quantity of the heating unit 320 and the second operation unit 330.

The second sensing unit 242 may sense the amount of deformation of the second operation unit 330. The second sensing unit 242 may convert the sensed amount of deformation of the second operation unit 330 into electric signals, and provide the electric signals converted from the amount of deformation of the second operation unit 330 to the second power adjustment unit 244 that will be explained hereinbelow.

The second power adjustment unit 244 is an apparatus or circuit configured to supply electric energy to the heating unit 320, and there is no particular limitation to its configuration.

The second power adjustment unit 244 may be connected to the second sensing unit 242. The second power adjustment unit 244 may be provided with the electric signals converted from the sensed information from the second sensing unit 242. The second power adjustment unit 244 may adjust the electric energy based on the electric signals converted from the sensed information, and apply the adjusted electric energy to the aforementioned heating unit 320.

Herein, the electric signals converted from the sensed information may include electric signals converted from the amount of deformation of the second operation unit 330.

The second power adjustment unit 244 may include a second power control unit 244-1, second power conversion unit 244-2, second battery 244-3, and second power distribution unit 244-4. The second power adjustment unit 244 may further include a second battery charging unit 244-5.

The second power control unit 244-1 may be connected to the second sensing unit 242. The second power control unit 244-1 may be provided with the electric signals converted from the sensed information from the second sensing unit 242. Herein, the electric signals converted from the sensed information may include electric signals converted from the amount of deformation of the second operation unit 330.

The second power control unit 244-1 may compare the electric signals converted from the sensed information with reference signals, and generate a second control signal according to the result of comparison. That is, the second power control unit 244-1 may generate the second control signal through a feedback control. The feedback control may include at least one control method of a proportional control (P control), integral control (I control), and differential control (D control). Furthermore, the second power control unit 244-1 may provide the second control signal to the second power conversion unit 244-2 that will be explained hereinbelow.

The second power control unit 244-1 may generate the second control signal through the aforementioned feedback control, but there is no limitation, and thus any control method may be used.

The second power conversion unit 244-2 may be connected to the second power control unit 244-1 and second battery 244-3. The second power conversion unit 244-2 may be provided with the second control signal from the second power control unit 244-1. The second power conversion unit 244-2 may convert the power of the second battery 244-3 based on the second control signal, and generate electric energy that corresponds to the converted power. Herein, the second power conversion unit 244-2 may include a DC-DC converter. Herein, the electric energy may include a voltage or current. Furthermore, the second power conversion unit 244-2 may apply the electric energy to the heating unit 320 or to the second power distribution unit 244-4 that will be explained hereinbelow.

The second power distribution unit 244-4 may be connected to the second power conversion unit 244-2. The second power distribution unit 244-4 may be provided with electric energy from the second power conversion unit 244-2. The second power distribution unit 244-4 may distribute the electric energy and generate adjusted electric energies of different sizes. Herein, the second power distribution unit 244-4 may include a Switching Mode Power Supply (SNIPS). Furthermore, the second power distribution unit 244-4 may apply the adjusted electric energies to the heating unit 320.

The second battery charging unit 244-5 may be connected to an external power source. The second battery charging unit 244-5 may be provided with charging energy from the external power source. Herein, the charging energy may include a current or voltage. Furthermore, the second battery charging unit 244-5 may charge the second battery 244-3 based on the charging energy.

The control unit 340 may be configured to include the first control unit 140 and the second control unit 240 separately, but there is no limitation, and thus as long as it may apply electric energy to the first operation unit 310 and the heating unit 320, respectively, the control unit 340 may be configured as one integrated component.

FIGS. 10A and 10B are views of an artificial muscle where relaxation/contraction-deformation occurs according to the embodiment of the present disclosure being applied to an arm.

FIG. 10A is a view of an artificial muscle when relaxation-deformation occurred according to the embodiment of the present disclosure, and FIG. 10B is a view of an artificial muscle when contraction-deformation occurred according to the embodiment of the present disclosure.

Referring to FIGS. 10A and 10B, the artificial muscle 300 according to the embodiment of the present disclosure has a hybrid actuator structure where the first operation unit 310 including electro-active polymer that generates relaxation-deformation, and the second operation unit 330 that has its basis on a yarn structure generating contraction-deformation are operated in an interlocked manner.

The hybrid actuator structure according to the embodiment of the present disclosure is capable of generating both the relaxation-deformation that requires a small amount of force and precise movement and also the contraction-deformation that requires a strong force, and may thus selectively realize endurance movement, short highly-intensive movement, or instant explosive movement of a muscular fiber that forms the human body muscle.

Herein, the hybrid actuator structure according to the embodiment of the present disclosure may be designed to provide various performances (forces) according to the purpose of use, by adjusting the number of electro-active polymer layers to be included in the first operation unit 310 or the properties of the electro-active polymer to be included in the electro-active polymer layers, or by adjusting the rigidity of the materials that form the second operation unit 330 having a yarn structure or the density of the materials.

Figure 11:
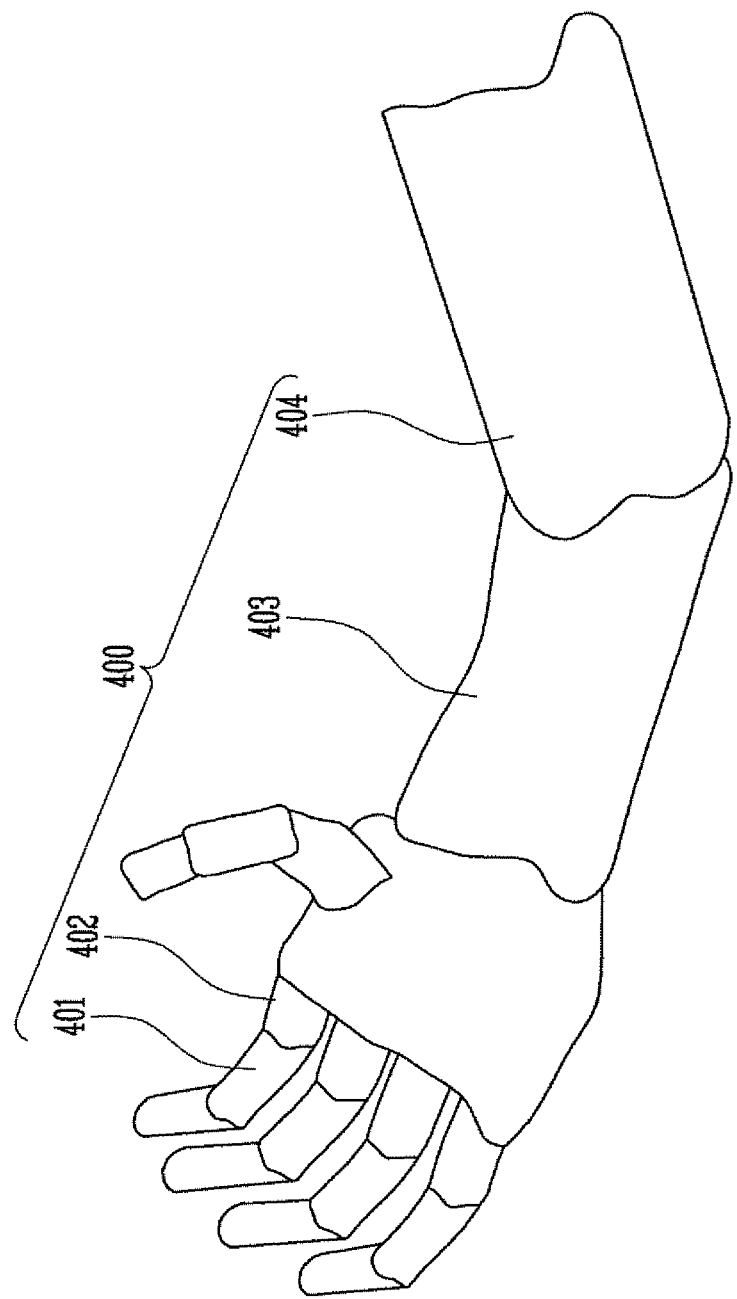
FIG. 11 is a view of the artificial muscle where relaxation/contraction-deformation occurs applied to a robot arm according to an embodiment of the present disclosure.

FIG. 11 is a view of the artificial muscle where relaxation/contraction deformation occurs according to the embodiment of the present disclosure being applied to a robot's arm.

Referring to FIG. 11, the artificial muscle where relaxation/contraction deformation occurs according to the embodiment of the present disclosure may be miniaturized and is flexible, and may thus be applied to a human-friendly life type robot that consists of a plurality of joints and that requires delicate movements.

Herein, in realizing a robot's movement, the artificial muscle according to the embodiment of the present disclosure may be disposed in the illustrated joints 401, 402, 403, 404 of the robot's arm 400 in singular or plural number in consideration of the type of force (for example, endurance movement, short highly-intensive movement, or instant explosive movement) needed in the joint(s) of the robot 400. Furthermore, the artificial muscle according to the embodiment of the present disclosure may selectively operate at least one operation unit of the first operation unit 310 that includes the electro-active polymer that generates relaxation-deformation and the second operation unit 330 that has its basis on a yarn structure that generates contraction-deformation.

Especially, the first operation unit 310 that includes the electro-active polymer and the second operation unit 330 that has its basis on a yarn structure are feedback-controlled in an interlocked manner with the control unit 340, and thus are capable of performing situation-recognition type movements where various external variables in the robot's movements are provided as feedbacks.

As aforementioned, the artificial muscle according to the embodiment of the present disclosure relates to an active artificial muscle that is capable of mimicking the characteristics of a muscle (consisting of muscle fiber, motor nerves/centers, spins, Golgi bodies and blood vessels) that is in charge of human body movements.

That is, the artificial muscle according to the embodiment of the present disclosure may perform relaxation/contraction movements through the first operation unit that includes the electro-active polymer, and the second operation unit that includes polymer material and/or nano-material that has its basis on a yarn structure. Furthermore, the artificial muscle according to the embodiment of the present disclosure may selectively control relaxation/contraction movements regarding the first operation unit and second operation unit through the control unit in response to the necessary power output of the muscle.

Therefore, compared to a conventional artificial muscle that uses oil pressure and that has excellent response characteristics but cannot be easily miniaturized since large-scale pneumatic equipments are needed in order to provide high performances, the artificial muscle according to the embodiment of the present disclosure includes a first operation unit and second operation unit configured based on polymer material and/or nano-material having excellent flexibility and elasticity, and thus may be miniaturized and further improve flexibility.

Furthermore, although a conventional artificial muscle using shape memory alloy may generate high power output, since its operation is based on transformation by heat, it has poor environmental resistance due to its sensitivity to external temperature, and is thus incapable of realizing precision movements. On the other hand, the artificial muscle according to the embodiment of the present disclosure consists of the first operation unit that includes electro-active polymer that generates relaxation-deformation, the second operation unit that has its basis on a yarn structure that includes polymer material and/or nano-material that generates contraction-deformation, and the control unit that selectively controls relaxation/contraction movement regarding the first operation unit and second operation unit in response to the necessary power output of the muscle, and thus the artificial muscle according to the embodiment of the present disclosure is capable of selectively performing relaxation/contraction movements according to the necessary power output of the muscle.

Furthermore, the artificial muscle according to the embodiment of the present disclosure may be applied to a muscle and/or robot (consisting of muscle fiber, motor nerves/centers, spins, Golgi bodies and blood vessels) that is in charge of human body movements. Especially, the artificial muscle according to the embodiment of the present disclosure may be applied to recyclable medical equipments, precision robots, and life support robots.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. An artificial muscle comprising:
an operation unit configured to include an electro-active polymer which generates relaxation-deformation based on applied electric energy;
a deformation restoration unit configured to restore the operation unit with the relaxation-deformed electro-active polymer; and
a control unit configured to apply the electric energy to the operation unit,
wherein the operation unit comprises:
an electro-active polymer layer that includes the electro-active polymer;
upper and lower electrode layers disposed on upper and lower parts of the electro-active polymer layer, respectively, the upper and lower electrode layers receiving the electric energy; and
upper and lower insulation layers disposed on an upper part of the upper electrode layer and on a lower part of the lower electrode layer, respectively, the upper and lower insulation layers insulating the upper electrode layer and the lower electrode layer, respectively.

2. The artificial muscle of claim 1,
wherein the electro-active polymer layer comprises at least one thin film type electro-active polymer layer.

3. The artificial muscle of claim 1,
wherein the operation unit has a shape of a tube.

4. The artificial muscle of claim 3,
wherein the deformation restoration unit is disposed inside the operation unit, and includes a spring.

5. The artificial muscle of claim 1,
wherein the control unit comprises:
a sensing unit configured to sense an amount of deformation of the operation unit; and
a power adjustment unit configured to adjust the electric energy based on the sensed amount of deformation of the sensing unit.

6. An artificial muscle comprising:
a heating unit configured to generate heat energy based on applied electric energy;
an operation unit configured to have a yarn structure where contraction-deformation occurs based on the heat energy generated in the heating unit; and
a control unit configured to apply the electric energy to the heating unit.

7. The artificial muscle of claim 6,
wherein the heating unit comprises a spring.

8. The artificial muscle of claim 7,
wherein the operation unit is disposed inside the heating unit.

9. The artificial muscle of claim 7,
wherein the spring has a hollow shape that allows a cooling fluid to flow.

10. The artificial muscle of claim 6,
wherein the control unit comprises:
a sensing unit configured to sense an amount of deformation of the operation unit; and
a power adjustment unit configured to adjust the electric energy based on the sensed amount of deformation of the sensing unit.

11. An artificial muscle comprising:
a first operation unit configured to include an electro-active polymer which generates relaxation-deformation based on applied electric energy;
a heating unit configured to generate heat energy based on applied electric energy;
a second operation unit configured to have a yarn structure where contraction-deformation occurs based on the heat energy generated in the heating unit; and
a control unit configured to apply the electric energy to the first operation unit and the heating unit.

12. The artificial muscle of claim 11,
wherein the first operation unit comprises:
an electro-active polymer layer configured to include the electro-active polymer;
an upper and lower electrode layer disposed on an upper part and a lower part of the electro-active polymer layer, respectively, the upper and lower electrode layer receive the electric energy; and
an upper and lower insulation layer disposed on an upper part of the upper electrode layer and a lower part of the lower electrode layer, respectively, the upper and lower insulation layer insulate the upper electrode layer and the lower electrode layer, respectively.

13. The artificial muscle of claim 12,
wherein the electro-active polymer layer comprises at least one thin film type electro-active polymer layer.

14. The artificial muscle of claim 11,
wherein the first operation unit has a shape of a tube.

15. The artificial muscle of claim 14,
wherein the heating unit is disposed inside the first operation unit, and comprises a spring.

16. The artificial muscle of claim 15,
wherein the second operation unit is disposed inside the heating unit.

17. The artificial muscle of claim 15,
wherein the spring has a hollow shape that allows a cooling fluid to flow.

18. The artificial muscle of claim 15,
wherein the spring comprises a hollow cylindrical shape.

19. The artificial muscle of claim 11,
wherein the control unit comprises:
a first control unit configured to sense an amount of deformation of the first operation unit, and adjust the electric energy being applied to the first operation unit based on the sensed amount of deformation of the first operation unit; and a second control unit configured to sense an amount of deformation of the second operation unit, and adjust the electric energy being applied to the heating unit based on the sensed amount of deformation of the second operation unit.

* * * * *